United States Patent [19]

Stein

[11] Patent Number: 5,571,196
[45] Date of Patent: Nov. 5, 1996

[54] PATELLO-FEMORAL JOINT REPLACEMENT DEVICE AND METHOD

[76] Inventor: Daniel Stein, 2415 Buckeye St., Newport Beach, Calif. 92660

[21] Appl. No.: 328,140

[22] Filed: Oct. 24, 1994

[51] Int. Cl.$^6$ ...................................................... A61F 2/38
[52] U.S. Cl. ................................................................ 623/20
[58] Field of Search ........................................ 623/18, 20

[56] References Cited

U.S. PATENT DOCUMENTS

| | | |
|---|---|---|
| 3,806,961 | 4/1974 | Müller . |
| 3,878,566 | 4/1975 | Bechtol ...................................... 623/20 |
| 4,007,495 | 2/1977 | Frazier . |
| 4,151,615 | 5/1979 | Hall . |
| 4,470,158 | 9/1984 | Pappas et al. .............................. 623/18 |
| 4,538,306 | 9/1985 | Dörre et al. ................................ 623/20 |
| 4,838,891 | 6/1989 | Branemark et al. . |
| 4,944,761 | 7/1990 | Stuhmer et al. ........................... 623/23 |
| 5,024,670 | 6/1991 | Smith et al. . |
| 5,176,684 | 1/1993 | Ferrante et al. ........................... 606/86 |
| 5,181,924 | 1/1993 | Geschwend et al. ...................... 623/20 |
| 5,397,360 | 3/1995 | Cohen et al. ............................... 623/16 |

FOREIGN PATENT DOCUMENTS

| | | | |
|---|---|---|---|
| 0336861 | 10/1989 | European Pat. Off. ................. | 623/20 |
| 2440185 | 7/1980 | France ...................................... | 623/20 |
| 3305237 | 8/1983 | Germany ................................. | 623/20 |

*Primary Examiner*—Michael J. Milano
*Attorney, Agent, or Firm*—Price, Gess & Ubell

[57] ABSTRACT

A prosthetic system comprising a patellar unit to replace the femoral surface of the patella with a convex prosthesis constructed from a low-friction material and an elongate femoral prosthesis for replacing the trochlear groove. The femoral prosthesis has a trough-like indentation on its upper surface to accommodate the patellar prosthesis and a lower surface with protruding vanes. The lower surface and the vanes are made of a biocompatible material that promotes bonding to living bone. The femoral prosthesis is inserted by first driving a guide rod into the distal end of the femur. Then a guide frame is inserted onto the rod to guide an instrument in the cutting of a groove in the trochlear portion of the femur. Then a second guide frame replaces the first guide frame acting as a template of cutting slots sized to receive the vanes of the prosthesis. Finally, the guide frame and rod are removed, and the prosthesis is pressed into the cut groove with the vanes occupying the slots. The prosthesis is fixed in place with an insertable peg. Over time the interaction of the bone with the vanes results in tight integration of the prosthesis so that it cannot not be loosened.

9 Claims, 2 Drawing Sheets

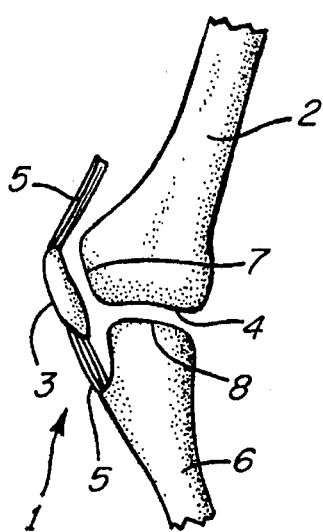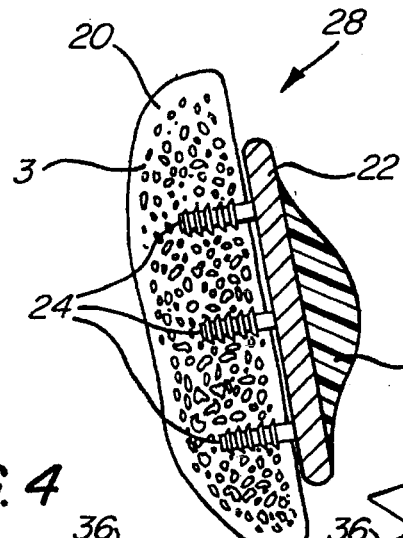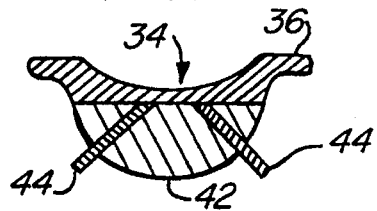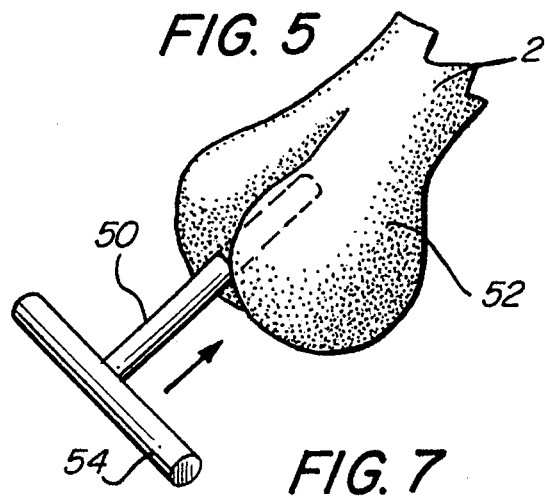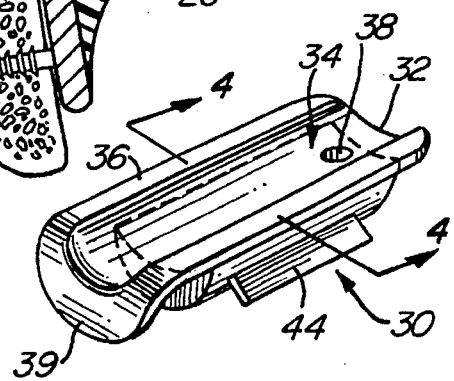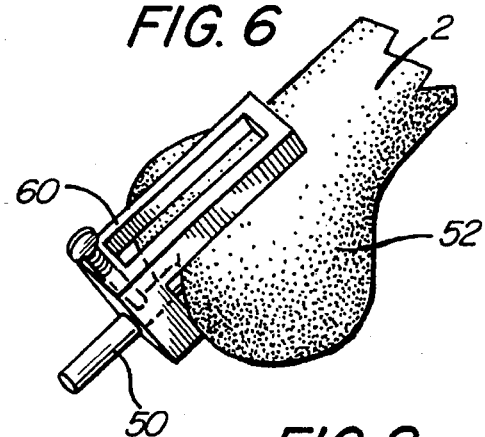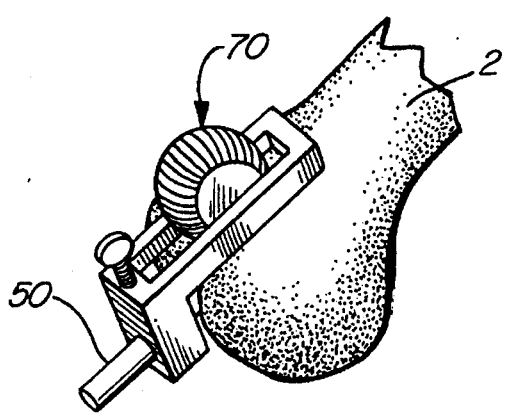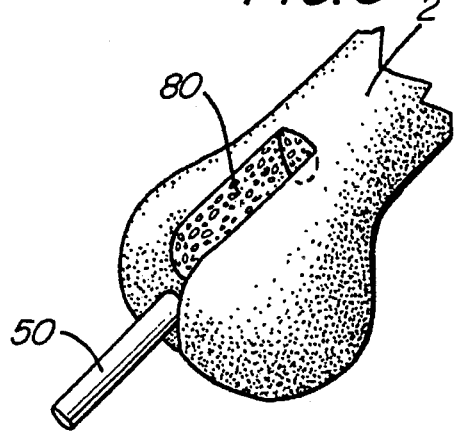

PATELLO-FEMORAL JOINT REPLACEMENT DEVICE AND METHOD

BACKGROUND OF THE INVENTION

1. Field of the Invention

The present invention relates generally to prosthetic replacements of joints and, more specifically, to an implantable patello-femoral joint prosthesis and method for its insertion.

2. Description of Related Art

Although joints of the human body are miraculous mechanical devices often lasting a lifetime with no added lubrication or service, our joints, like any mechanical or biological structure, are subject to certain failures. The joints are naturally lubricated and cushioned by synovial membranes and cartilages so that they are normally subject to little wear. Part of this apparent lack of wear is doubtless due to the living tissue's ability of regeneration and self-repair. Sometimes the body's immune system goes awry and attacks a joint, thereby damaging it irreversibly (rheumatoid arthritis). Sometimes old age and general wear and tear catches up with the joint's biological repair system (osteoarthritis). Sometimes a sharp blow or overextension of the joint results in mechanical damage that cannot be repaired by the normal healing process.

The knee joint is a frequent place for joint damage, and inability to walk normally is a frequent result of such damage. The knee is a common source of problems because the joint has an unusually large range of motion and bears half the weight of the entire body. A primary knee movement is the bending and straightening of the leg in which a lower part of the leg (tibia and fibula bones) flex in relation to an upper part of the leg (femur bone). The knee joint flexes over almost 180 degrees from a kneeling position, where the upper and lower leg are almost parallel to each other, to a straight position, where the upper and lower leg form essentially a straight line. The knee joint can also accommodate a certain amount of rotary motion in which the lower leg rotates a few degrees in relation to the upper leg.

This wide range of motion requires extensive contact surface between the femur and the tibia. The joint is rather loosely held together by tendons and ligaments to permit such a wide range of motion. A front-facing side of the knee joint is protected by a separate knee cap (patella) which is held in place by ligaments and slides over a femoral joint surface as the knee bends. The patella and its ligaments are mechanically involved in joint extension. If any of the joint surfaces (femoral surface, patellar surface, or tibial surface) becomes damaged or roughened, the knee joint will not operate properly.

A common problem is damage to the patello-femoral joint so that free motion of the patella is inhibited and painful. This "runner's knee" can make normal joint movement almost impossible. At one time, before the mechanical and protective functions of the patella were understood, the patella was simply removed in an attempt to cure patello-femoral problems.

Today a variety of prosthetic replacements have been developed for different joint surfaces of the knee joint. In extreme cases the entire joint can be replaced with a prosthetic device. However, such surgery naturally requires a considerable time for recovery. In less extreme cases it may be advantageous to replace only the damaged part of the joint. The present invention is concerned with such a replacement for the patello-femoral joint. This type of knee surgery is less drastic than a complete replacement of the knee. It is designed for patients whose main problems involve only the patello-femoral part of the knee and is directed to providing a smooth replacement surface on the femur on which the patella "rides."

There are a number of prior art devices which have attempted to solve the problem of replacing the trochlear groove, or in some way attempted to solve problems due to improper interaction of the patella and femur. U.S. Pat. No. 3,806,961 to Müller shows a prosthesis in which an annular sector having a guide groove is implanted into the end of the femur. A raised arcuate runner member is implanted into the patella so that the patella can slidably move in the guide groove with the runner member acting as a bearing surface. The prostheses are attached to the bone surfaces by bone cement and by pin-like protrusions that extend into channels cut into the bone. A basic problem with bone cement is that it is not always permanent. A layer of inflammatory tissue forms between the bone and the cement so that the implant eventually loosens.

U.S. Pat. No. 3,878,566 to Bechtol discloses another patellar prosthesis. Here a femoral implant bears a more or less acute groove, and the patellar component bears a somewhat crest-like ridge projection that rides in the groove. Again, the devices are fixed in place with bone cement, although they also bear ridged pegs designed to allow improved bone adhesion. U.S. Pat. No. 4,007,495 to Frazier uses a slightly different approach. The patellar component rides in a femoral groove, but the system is also equipped with a femoral projection that engages a slot in the patellar implant. While this structure prevents separation of the patella from the femur, it also greatly restricts movement of the patella and may result in unnatural joint action. Again, this prosthesis is attached by bone cement and ridged pegs.

U.S. Pat. No. 4,151,615 to Hall provides a femoral component and a patellar component that more closely approximate natural patello-femoral joint motion. However, this device is also designed to rely on bone cement and pegs for adherence to the bones of the joint. U.S. Pat. No. 4,838,891 addresses the adhesion problems of prior prostheses by providing a two-part system where an anchoring device is inserted during a first operation. After the healing process fixes the anchoring device firmly in place, a second operation inserts the weight-bearing part of the prosthesis which engages the anchoring device. However, this system requires multiple operations even to insert a patello-femoral prosthesis-a prosthesis designed to be used in relatively uncomplicated cases.

OBJECTS AND SUMMARY OF THE INVENTION

It is an object of the present invention to provide a patello-femoral replacement device that allows essentially normal movement of that joint;

It is another object of the present invention to provide a prosthesis with improved adherence to the bone without the use of bone cement; and It is a further object of the present invention to provide a method for the easy insertion of the patello-femoral prosthesis.

These and additional objects are met by the use of a prosthetic system comprising a patellar prosthesis and a femoral prosthesis. The patellar prosthesis replaces the femoral surface of the patella with a convex prosthesis constructed from a low-friction material. The femoral prosthesis replaces the trochlear groove of the femur with an elongate prosthesis having a trough-like indentation in its upper surface for the patellar prosthesis to ride in. The femoral prosthesis has vanes protruding from a lower surface thereof. The vanes and the lower surface are of a biocompatible material that promotes bonding to living bone. The femoral prosthesis is inserted by first driving a guide rod into the distal end of the femur. The rod is then used to position a guide frame which directs an instrument in cutting a groove in the trochlear portion of the femur. Then a second guide frame replaces the first frame and is used as a template for cutting slots sized to receive the vanes of the prosthesis. Finally, after removing the frame and rod, the prosthesis is pressed into the cut groove with the vanes occupying the slots. The prosthesis is fixed in place with an implant peg, and over time the interaction of the bone with the vanes results in tight integration of the prosthesis so that it cannot become loosened.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 1 is a diagrammatic view of a cross-section of a distal end of a human femur showing the knee joint;

FIG. 2 shows a cross-sectional view of a patellar prosthesis used in the present invention;

FIG. 3 shows a perspective view of an upper surface of a femoral prosthesis of the present invention;

FIG. 4 shows a cross-section of the prosthesis of FIG. 3;

FIG. 5 illustrated insertion of a guide rod according to the method of the present invention;

FIG. 6 illustrates insertion of a router guide frame of the method of the present invention;

FIG. 7 illustrates the use of the router guide frame of FIG. 6;

FIG. 8 shows the effect of the router;

DETAILED DESCRIPTION OF THE PREFERRED EMBODIMENTS

Figure 9:
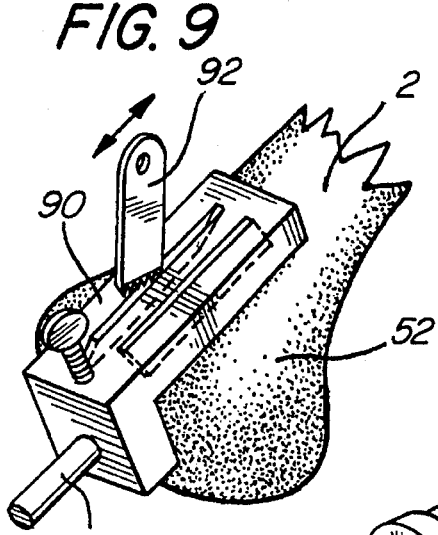
FIG. 9 illustrates insertion and use of a vane guide frame of the method of the present invention.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a patello-femoral prosthesis to replace the patello-femoral surfaces of a knee joint.

FIG. 1 shows a diagram of the distal end of a human femur 2. As already explained, a chlondylar region 4 of the femur 2 interacts with a proximal region 8 of the tibia 6 to comprise the knee joint 1. The knee joint 1 also comprises a separate patella 3 or knee cap which is held in place by tendons and ligaments 5. The patella 3 forms part of the mechanical structure of the joint as the various tendons transfer mechanical forces from the muscles (not shown) to the patella 3. The patella 3 moves in relation to the bones of the leg by sliding up and down in a trochlear groove 7 as the knee flexes and extends.

The present invention is directed towards solving knee problems caused by a loss of smooth unimpeded patellar sliding. The invention entails replacement of an undersurface of the patella 3 with a low-friction surface which slides in a trough-like prosthesis that replaces the trochlear groove 7 in the distal end 4 of the femur 2. Replacement of the patellar surface is well known in the art and is briefly illustrated only for the sake of completeness.

The femoral surface 20 (FIG. 2) of the patella 3 is resected to remove any damaged tissue and to compensate for an increase of apparent patellar thickness caused by the addition of the prosthesis. The prosthetic device 28 used is shown in FIG. 2. A disc-shaped base 22 bears peg-like protrusions 24. The base and protrusions are made from a biocompatible material, preferably a metal, such as titanium, that can become integrated with living bone. The protrusions 24 bear ridges or other modifications to maximize their surface area and, hence, their interaction with the bone.

The base 22 is generally round in shape and has a convex surface 26 sized to fit the femoral prosthesis 30. The femoral surface of the base 22 is covered by a low-friction plastic material such as UHMWPe (ultra high molecular weight polyethylene), which is also biocompatible. This material is joined to the base by some type of mechanical interaction. One possible method of attachment is taught by U.S. Pat. No. 5,024,670 to Smith et al. It is important that the UHMWPe surface be convex to ride in a trough-like indentation of a femoral prosthesis. The convex surface 26 may be entirely provided by the plastic material in which case the underlying base 22 would be planar as illustrated, or the plastic material may simply overlay and mimic the shape of a convex base (not illustrated).

The femoral prosthesis 30, as shown in FIG. 3, is an improved device unique to the present invention. The device comprises an elongate member 32 with a trough-like indentation 34 in its upper surface. The indentation 34 is arcuate in cross-section (see FIG. 4). As already mentioned, the prosthesis 30 is intended to replace the trochlear groove in which the patella 3 normally rides. To this end, at least a lower surface 42 of the prosthesis 30, which contacts the living bone of the femur 2, is constructed of cobalt chromium alloy or some other biocompatible material that is capable of forming a strong union with bone. To further enhance interaction between the prosthesis 30 and the femur 2, the device bears at least two longitudinally-oriented, non-parallel vanes 44 that project out about 2–3 cm from the elongate member 32. The vanes 44 spreading apart for preventing the elongate member 32 from being lifted from the femur 2.

An upper surface of the prosthesis 30 bears a longitudinal trough-like indentation 34. The upper surface is preferably constructed from or coated with chromium or some other hard, wear-resistant material. In cross-section (FIG. 4) the trough-like indentation 34 is fairly shallow. The prostheses 30 are available in various sizes depending on the size of the knee joint to be replaced. However, the average dimensions of the indentation 34 are about 3 cm wide by 8 cm long. Margins of the groove form a relatively flat lip 36. If the edges of the trough-like indentation 34 ended abruptly without the lip 36, the patellar prosthesis 28 might overrun the edge of the femoral prosthesis 30 during abnormal overextension or manipulation of the joint. Instead, the patellar prosthesis 28 merely rides on the flat lip 36 and is returned to the indentation 34 by ligaments and tendons 5 when the abnormal conditions cease.

At a proximal end of the indentation 34 the prosthesis 30 bears an aperture 38 for the insertion of a locking implant peg. The peg (see FIG. 12) is preferably spring-loaded so that when it is inserted through the aperture 38 and tightened, it locks in place, thereby resisting accidental loosening. The implant peg is intended to mechanically fix the prosthesis 30 in place until the bone forms a strong union with the undersurface 42 of the prosthesis 30.

At a distal end the prosthesis is turned down almost at right angles to the elongate indentation. This downturned region 39 serves a function similar to the lip 36 along the edges of the trough-like indentation 34. Normally the patellar prosthesis 28 slides up and down in the indentation 34. The proximal end of the prosthesis 30 extends far enough up the femur 2 that it is impossible for the patellar prosthesis 28 to run off that end. However, it may be possible, under extreme conditions of joint motion, for the patellar prosthesis 28 to move past the distal end of the indentation 34. The downturned end 39 of the prosthesis 30 provides a smooth ramp for the patellar prosthesis 28 to return to the indentation 34 without becoming stuck at the distal end of the femoral prosthesis 30.

The prosthesis 30 is installed into the femur 2 according to the following procedure. After resection of the knee joint 1 to expose the trochlear end 52 of the femur 2, a guide rod 50 is driven into the distal end of the femur 2 (see FIG. 5). A removable handle 54 aids in this process. The rod 50 is oriented parallel to a long axis of the femur 2 and serves to position several apparatuses used to install the prosthesis 30.

Next, a router guide frame 60 (see FIG. 6) is inserted onto the guide rod. The guide frame 60 acts as a template which guides a router 70 which excavates the trochlear groove to make room for the prosthesis 30. After the router 70 has been used, the trochlear groove will have become an enlarged groove 80 of sufficient size to accommodate the elongate the femoral prosthesis 30.

The router guide frame 60 is removed and replaced with a vane guide frame 90 (see FIG. 9). This frame 90 fits into the excavated groove 80 and is designed to guide a bone cutting saw 92 in cutting narrow channels that are just the size and shape of the prosthesis vanes 44. After the bone cutting saw 92 is used, the vane guide frame 90, as well as the guide rod 50, are removed, leaving an enlarged trochlear groove 80 including narrow channels 100 cut into the groove 80 and sized to accommodate the vanes 44 of the prosthesis 30.

Figure 10:
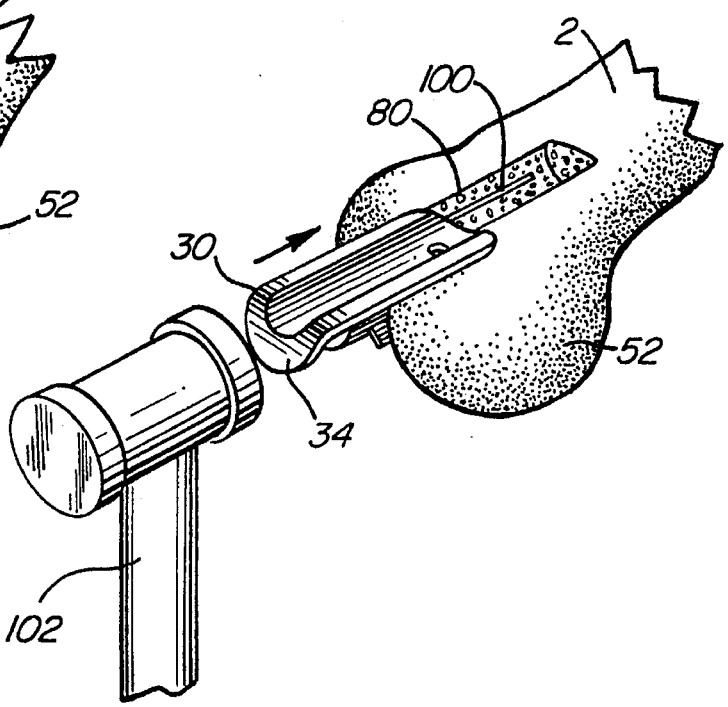
FIG. 10 illustrates insertion of the femoral prosthesis of the present invention.
Figure 11:
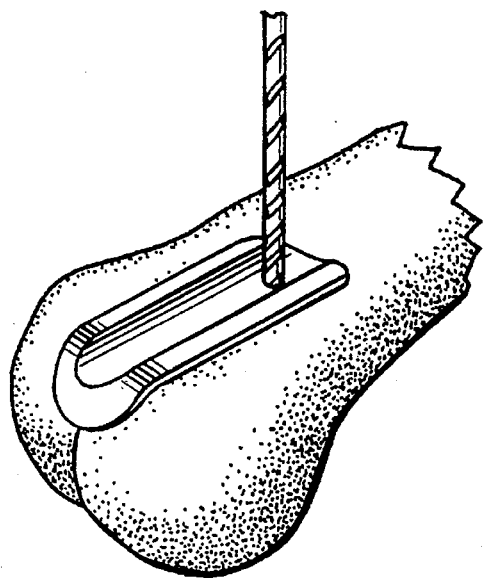
FIG. 11 shows drilling a hole for an implant peg.
Figure 12:
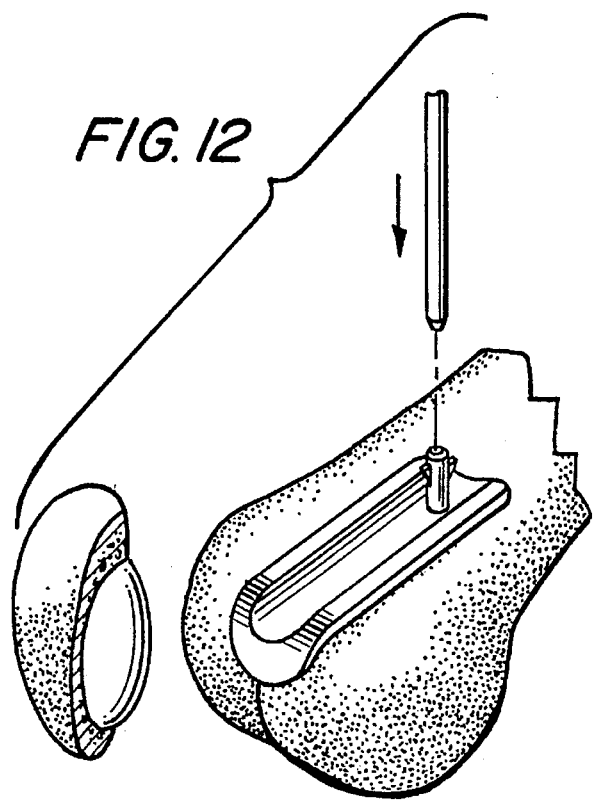
FIG. 12 illustrates fixing the femoral prosthesis with the implant peg.

As shown in FIG. 10, the proximal end of the prosthesis 30 is inserted into the distal of the machined trochlear groove 80. The prosthesis 30 just fits with the vanes 44 slipping into the channels 100. Not only are the vanes 44 and channels 100 designed to increase the surface area for a bone union to form; they also ensure the proper orientation of the prosthesis 30. The non-parallel vanes 44 and channels 100 make it impossible for the prosthesis 30 to be inserted incorrectly or for the prosthesis 30 to shift or loosen after insertion. A small mallet 102 is then used to strike the downturned distal end 39 of the prosthesis 30, driving the prosthesis 30 all the way into the machined groove 80 with the downturned end 39 contacting the distal end of the femur 2. Drilling a hole in the bone (FIG. 4) followed by insertion of the locking implant peg 110 completes the insertion procedure (FIG. 12).

If the patellar unit 28 has not already been installed, it is installed at this juncture. The patella 3 is then reinserted into the new trochlear groove (trough-like indentation 34) and the joint is closed. No bone cement is necessary, so there is no danger of forming a barrier of connective tissue between the cement and the prosthesis. Because there is rigid fixation, the danger of loosening is minimized. In any case, the vanes 44 ensure that the only way to remove the prosthesis 30 is to exert a force parallel to the long axis of the femur and away from the body. The locking implant peg 110 effectively resists any tendency towards a distal sliding of the prosthesis 30. In a relatively short time a union between the titanium of the prosthesis 30 and the femur 2 is formed. This union makes it virtually impossible to loosen the prosthesis 30, even without the locking implant peg 110.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A patello-femoral prosthesis system for replacing articulating surfaces of a patello-femoral joint, the prosthesis system comprising:

a patellar component dimensioned and arranged to be attached to a surface of a patella and dimensioned and arranged for facing a surface of a femur, the patellar component comprising:

a disc-shaped attachment piece including a plurality of pegs on a patellar surface thereof for insertion into a patella; and a bearing piece attached to a femoral surface of the attachment piece and presenting a smooth, convex surface; and an elongate femoral prosthesis arranged for attachment to a patellar surface of a femur and dimension for replacing a trochlear groove thereof, the femoral prosthesis comprising:

an outer surface for facing a patella, the outer surface bearing a shallow, cross-sectionally arcuate indentation running the length of the outer surface parallel to a long axis of a femur when the femoral prosthesis is attached thereto;

out-turned lips forming longitudinal edges of the outer surface of the femoral prosthesis;

a proximal end spaced from a tibial end of a femur when the femoral prosthesis is attached thereto, the proximal end bearing an insertable peg for attaching the femoral prosthesis to a femur and preventing accidental loosening; and a distal end near a tibial end of a femur when the femoral prosthesis is attached thereto, the distal end forming a downturned edge to keep the bearing piece of the patellar component from becoming trapped;

a convex inner surface sized to fit an enlarged trochlear groove; and at least two projecting vanes, spreading apart and non-parallel cross-sectionally, borne on the inner surface, running a length thereof and arranged and dimensioned to fit slots cut in a femur, for ensuring permanent adhesion of the femoral prosthesis by directly contacting bone when the femoral prosthesis is affixed to a femur.

2. The prosthesis system of claim 1, wherein at least the inner surface and vanes of the femoral prosthesis are constructed of a biocompatible material that promotes union to bone.

3. The prosthesis system of claim 1, wherein the insertable peg is of a self-locking design so that it cannot become loosened after being once locked in place.

4. A patello-femoral prosthesis for replacing a femoral surface of a patello-femoral joint and dimensioned and arranged for replacing a trochlear groove, the prosthesis comprising:

an elongate member comprising:

an outer surface facing a patella when the prosthesis is in use, the outer surface bearing a shallow, cross-sectionally arcuate indentation running the length of the outer surface parallel to the long axis of a femur when the prosthesis is attached thereto;

a proximal end spaced from a tibial end of a femur when the femoral prosthesis is attached thereto, the proximal end bearing an insertable peg for attaching the femoral prosthesis to a femur preventing accidental loosening; and an inner surface facing a femur when the prosthesis is attached thereto, the inner surface composed of biocompatible material, and sized to fit an enlarged trochlear groove; and at least two vanes, spreading apart and non-parallel cross-sectionally, projecting from the inner surface of the prosthesis, the vanes running substantially a length thereof, and constructed of a biocompatible material for ensuring adhesion by directly contacting bone.

5. The prosthesis of claim 4, wherein the biocompatible material of the inner surface and the vanes is cobalt-chromium alloy.

6. The prosthesis of claim 4, wherein the insertable peg is of a self-locking design so that it cannot become loosened after being once inserted.

7. The prosthesis of claim 4, wherein the indentation is surrounded by a substantially flat out-turned lip for preventing a patellar prosthesis from overrunning a longitudinal edge of the femoral prosthesis.

8. The prosthesis of claim 4, wherein the prosthesis also bears a downturned distal end for preventing a patellar prosthesis from overrunning the distal end of the femoral prosthesis.

9. A prosthesis for insertion into a femur to replace a femoral surface of a patello-femoral joint, the prosthesis being an elongate member comprising:

an outer surface facing a patella when the prosthesis is inserted into a femur, the outer surface bearing a shallow, cross-sectionally arcuate indentation running the length of the outer surface parallel to a long axis of a femur when the prosthesis is inserted therein, the indentation being surrounded by a substantially flat outturned lip for preventing a patellar prosthesis from overrunning a longitudinal edge of the femoral prosthesis;

a proximal end spaced from a tibial terminus of a femur when the prosthesis is inserted therein, the proximal end bearing an insertable locking peg for attaching the prosthesis to a femur and preventing accidental loosening; and a downturned distal end, opposite the proximal end, for preventing a patellar prosthesis from overrunning the distal end of the femoral prosthesis;

an inner surface facing a femur when the prosthesis is inserted into a femur, the inner surface composed of biocompatible titanium, and sized and arranged to slide longitudinally into a groove cut in a trochlear region of a femur; and two vanes, spreading apart and non-parallel to each other cross-sectionally, projecting from the inner surface of the prosthesis, the vanes running substantially a length thereof, and constructed of a biocompatible titanium for ensuring orientation of the prosthesis by fitting into slots cut in a femur and adhesion of the prosthesis by directly contacting bone.

* * * * *